United States Patent
Ferrari et al.

(10) Patent No.: US 6,846,950 B2
(45) Date of Patent: Jan. 25, 2005

(54) PROCESS FOR SYNTHESIS OF 1-(AMINOMETHYL)CYCLOHEXANE ACETIC ACID HYDROCHLORIDE

(75) Inventors: Massimo Ferrari, Cenate Sotto (IT); Marcello Ghezzi, Curno (IT); Paolo Belotti, San Paolo D'Argon (IT)

(73) Assignee: Erregierre S.p.A., San Paolo D'Argon (IT)

(*) Notice: Subject to any disclaimer, the term of this patent is extended or adjusted under 35 U.S.C. 154(b) by 107 days.

(21) Appl. No.: 10/420,154

(22) Filed: Apr. 22, 2003

(65) Prior Publication Data

US 2004/0063997 A1 Apr. 1, 2004

(30) Foreign Application Priority Data

Oct. 1, 2002 (IT) .................................... MI2002A2071

(51) Int. Cl.[7] .............................................. C07C 61/08
(52) U.S. Cl. ...................................................... 562/507
(58) Field of Search ......................................... 562/507

(56) References Cited

U.S. PATENT DOCUMENTS 4,024,175 A 5/1977 Satzinger et al.
4,152,326 A 5/1979 Hartenstein et al.
5,091,567 A 2/1992 Geibel et al.
5,362,883 A 11/1994 Jennings et al.
6,054,482 A 4/2000 Augart et al.

OTHER PUBLICATIONS

Abstract of US Patent: 5132451.
Abstract of US Patent: 5095158.
Abstract: Gabapentin—Drugs of the Future vol. 9. No. 6 1984.
Abstract of US Patent: 5068413.
Abstract of US Patent: WO 9828255.

*Primary Examiner*—Paul J. Killos
(74) *Attorney, Agent, or Firm*—Collard & Roe, P.C.

(57) ABSTRACT

A process for synthesis of 1-(aminomethyl)cyclohexane acetic acid hydrochloride (Gabapentin hydrochloride) comprising:
  a) Reaction of a mixture of acetic anhydride/ammonium acetate with 1,1-cyclohexane-diacetic acid to yield 3,3-pentamethylene glutarimide;
  b) Treatment of 3,3-pentamethylene glutarimide with sodium hydroxide in an aqueous solution up to dissolution, dripping the solution thus obtained into a sodium hydroxide/sodium hypochlorite mixture, which is also aqueous, followed by acidification with hydrochloric acid to yield gabapentine hydrochloride.

10 Claims, No Drawings

PROCESS FOR SYNTHESIS OF 1-(AMINOMETHYL)CYCLOHEXANE ACETIC ACID HYDROCHLORIDE

FIELD OF THE INVENTION

The present invention relates to a process for synthesis of 1-(aminomethyl)cyclohexane-acetic acid hydrochloride (GABAPENTIN hydrochloride).

PRIOR ART

GABAPENTIN, which is characterized by the following structural formula (I)

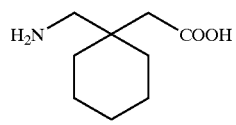

is an active principle mainly used in human therapy for treating cerebral disorders, such as epilepsy ("Drugs of the future", vol. 9, N° 6, 1984, pp. 418–419). There exist various processes, which are described in the prior art, for the synthesis of this molecule as free-base gabapentin. Amongst these processes, there are the ones described in the U.S. Pat. Nos. 5,132,451, 5,095,148, 5,068,413. Each of these methods involves the formation of a cyanic intermediate, which is subjected to hydrogenation in particularly severe conditions, which are impracticable at an industrial size for producing the free amino acid gabapentin.

A valid alternative, at an industrial size, for producing free-base gabapentin is its preparation starting from the corresponding hydrochloride salt, subtracting the chloride ion, to make available the molecule of gabapentin in the form of a free amino acid, according to techniques that are well known to the art (WO 98/28255).

Therefore the need was felt to provide new processes for synthesis of gabapentin hydrochloride that may be easely sealed up to industrial size, which are characterized by just a few steps of synthesis with high yields, starting from reagents that are readily available on the market, to yield gabapentin hydrochloride of high purity and in amounts such as to render industrially applicable the subsequent process of conversion from gabapentin hydrochloride to free-base gabapentin.

SUMMARY

A new process for the synthesis of gabapentin hydrochloride has now been found, via the formation of the intermediate: 3,3-pentamethylene glutarimide or 3-Azaspiro[5.5]-undecane-2,4-dione, just two steps of synthesis in conditions that are readily sealed up to industrial size, commercially available reagents, with yields of between 85% and 95% and an end product, gabapentin hydrochloride, of high purity (>95.5%, by HPLC).

The applicant has unexpectedly found a new process for synthesis of gabapentin hydrochloride, comprising:

Reaction of a mixture of acetic anhydride/ammonium acetate with 1,1-cyclohexane diacetic acid at 160° C.–170° C., followed by precipitation of the product by gradual cooling and treatment with water/secondary butyl alcohol, and subsequent filtration to yield 3,3-pentamethylene glutarimide;

Treatment of 3,3-pentamethylene glutarimide with sodium hydroxide in an aqueous solution up to dissolution, dripping the solution obtained into a sodium hydroxide/sodium hypochlorite mixture, which is also in an aqueous solution, followed by acidification with hydrochloric acid to yield gabapentin hydrochloride.

DETAILED DESCRIPTION OF THE INVENTION

The subject of the present invention is a process for the synthesis of gabapentin hydrochloride, comprising:

a) Reaction of a mixture of acetic anhydride/ammonium acetate with 1,1-cyclohexane diacetic acid to yield 3,3-pentamethylene glutarimide;

b) Treatment of 3,3-pentamethylene glutarimide with sodium hydroxide in an aqueous solution up to dissolution, dripping the solution obtained into a sodium hydroxide/sodium hypochlorite mixture, which is also aqueous, followed by acidification with hydrochloric acid to yield gabapentin hydrochloride.

The reaction of step a) is carried out at a temperature of 160° C. to 170° C., up to elimination by distillation of the acetic acid that has formed. Extinguishing of the reaction of step a) is achieved by gradual cooling, first at a temperature of 90° C.–110° C., with consequent addition to the reaction environment of a water/secondary butyl alcohol mixture, and subsequently, completing said cooling to room temperature. Extinguishing is completed by bringing the pH to a basic value; namely, a pH of approximately 9 is reached by treating with 30% of aqueous ammonia. Step a) according to the process object of the present invention leads to the synthesis of 3,3-pentamethyl glutarimide with an average yield of 95%.

In step b) the treatment of 3,3-pentamethyl glutarimide with sodium hydroxide in an aqueous solution is preferably carried out at a temperature of between 50° C. and 80° C., in water with 30% sodium hydroxide. The resulting solution is preferably treated with a sodium hydroxide/sodium hypochlorite mixture present at a temperature of between 0° C. and 50° C., more preferably of between 0° C. and 30° C., more in particular with a mixture wherein sodium hydroxide is 30% and sodium hypochlorite is 15%. Acidification, which is carried out at a temperature of between 0° C. and 50° C., preferably at room temperature, is preferably carried out using aqueous hydrochloric acid.

According to a further particularly preferred embodiment of the present invention, in step b), acidification with hydrochloric acid is followed by a treatment with an aqueous solution of sodium bisulphite, under stirring at 40° C.–60° C., up to complete elimination of the excess of chlorine, with recovery of the gabapentin hydrochloride by filtration at 0° C., washing with ethyl acetate.

Provided below are some purely illustrative and non-limiting examples of the present invention.

EXAMPLE 1

Preparation of 3,3-pentamethylene Glutarimide

A flask is charged with 66.5 g of acetic anhydride, 66.5 g of ammonium acetate, and 100 g of 1,1-cyclohexane diacetic acid. The reaction mass is heated to 160° C.–170° C. for eight hours, eliminating by distillation the acetic acid that has formed. It is cooled to 90° C.–110° C., and 200 g of water and 100 g of secondary butyl alcohol are added. It then undergoes further cooling to room temperature, and the pH is brought to approximately 9 using 30% of aqueous ammonia. This is followed by filtration, washing the solid with water. 87.7 g of dry 3,3-pentamethylene glutarimide are obtained (yield 97%).

EXAMPLE 2

Preparation of Gabapentin Hydrochloride

A flask is charged with 100 g of 3,3-pentamethylene glutarimide, 200 g of water, and 81 g of 30% sodium hydroxide. It is heated to 50° C.–80° C. for approximately two hours up to complete dissolution. The product is poured into a mixture consisting of 400 g of 15% sodium hypochlorite and 162 g of 30% sodium hydroxide, keeping the temperature of the system between 0° C. and 30° C. It is left to rest for approximately 3 hours at room temperature. The resulting solution is then poured into 32% hydrochloric acid. The excess of chlorine is decomposed by treatment with an aqueous solution of sodium bisulphite, followed by stirring at a temperature of 40°–60° C. for a few hours. Then it is cooled to approximately 0° C., filtering the solid and washing it with ethyl acetate. 95 g of gabapentin hydrochloride are obtained with a yield of 88% and a degree of purity, measured via HPLC, >99.5%.

EXAMPLE 3

Preparation of Gabapentin Form II 100 g of gabapentin hydrochloride are solubilized in 500 g of deionized water and 90 g of dicyclohexylamine are added while heating to 30°–50° C. An abundant precipitation of dicyclohexylamine hydrochloride is produced that is filtered with a Buchner funnel. The dicyclohexylamine hydrochloride solid is treated with sodium hydroxide, thus regaining the dicyclohexylamine that is thus recovered and recycled in the separation stage of the chloride ion by precipitation, while the aqueous solution contains gabapentin in free amino acid form.

The aqueous solution obtained by filtering is distilled under reduced pressure, until the start of precipitation, and the residue is taken back with ethyl alcohol, heated to 40°–50° C., and the suspension obtained is cooled for a few hours and filtered.

The solid obtained is vacuum dried at 30°–40° C., producing raw gabapentin in the polymorphic form "FORM II" with a formula (VI) impurity content of less than 0.05%. The yield is 80%.

50 g of raw gabapentin prepared as above described are suspended in 250 g of methyl alcohol and 125 g of isopropyl alcohol. It is heated under reflux for 30 minutes, and cooled at 20–25° C. for two hours and subsequently at 0° C. for a further two hours. The suspension is filtered with a Buchner funnel and is vacuum dried at 30°–40° C., producing gabapentin of polymorphic form "FORM II" with a HPLC purity greater than 99.85% a content of lactam<0.10% and a content of chloride anions<100 ppm.

What is claimed is:

1. A process for synthesis of gabapentin hydrochloride comprising:
    a) Reaction of a mixture of acetic anhydride/ammonium acetate with 1,1-cyclohexane diacetic acid to yield 3,3-pentamethylene glutarimide;
    b) Treatment of 3,3-pentamethylene glutarimide with sodium hydroxide in an aqueous solution up to dissolution, dripping the solution obtained into a sodium hydroxide/sodium hypochlorite mixture, which is also aqueous, followed by acidification with hydrochloric acid to yield gabapentine hydrochloride.

2. The process according to claim 1, wherein the reaction of step a) is conducted at a temperature of 160° C. to 170° C.

3. The process according to claim 1, wherein extinguishing of the reaction of step a) is achieved by gradual cooling, first at a temperature of 90° C.–110° C. with consequent addition to the reaction environment of a water/secondary butyl alcohol mixture, and subsequently, completing said cooling to room temperature, the pH being brought to a basic value; namely, a pH of approximately 9 is achieved by treating with 30% aqueous ammonia.

4. The process according to claim 1, wherein in step b) the treatment of 3,3-pentamethyl glutarimide with sodium hydroxide in an aqueous solution is carried out at a temperature of 50° C. to 80° C., in water with 30% sodium hydroxide.

5. The process according to claim 1, wherein in step b) the sodium hydroxide/sodium hypochlorite mixture consists of sodium hydroxide: 30% and sodium hypochlorite: 15%.

6. The process according to claim 1, wherein in step b) the treatment with sodium hydroxide/sodium hypochlorite occurs at a temperature of 0° C. to 50° C., more preferably of 0° C. to 30° C.

7. The process according to claim 1, wherein in step b) the acidification is carried out with aqueous hydrochloric acid.

8. The process according to claim 1, wherein in step b) the acidification is carried out at a temperature of 0° C. to 50° C., preferably at room temperature.

9. The process according to claim 1, wherein in step b) the acidification with hydrochloric acid is followed by a treatment with an aqueous solution of sodium bisulphite, under stirring at 40° C.–60° C., up to complete elimination of the excess of chlorine.

10. Gabapentin form II with a purity measured via HPLC>99.5%, a content of lactam<0.110% and a content of chloride anions<100 ppm, obtained from Gabapentin hydrochloride prepared according to the process of claim 1.

* * * * *